United States Patent

Potthast

[11] Patent Number: 5,936,406
[45] Date of Patent: Aug. 10, 1999

[54] METHOD FOR DETERMINING THE POSITION OF A LOCAL ANTENNA IN AN EXAMINATION CHAMBER OF A MAGNETIC RESONANCE APPARATUS

[75] Inventor: Andreas Potthast, Forchheim, Germany

[73] Assignee: Siemens Aktiengesellschaft, Munich, Germany

[21] Appl. No.: 08/995,317

[22] Filed: Dec. 22, 1997

[30] Foreign Application Priority Data

Dec. 20, 1996 [DE] Germany .................. 196 53 535.2

[51] Int. Cl.$^6$ ............................................. G01V 3/00
[52] U.S. Cl. ..................................... 324/318; 600/424
[58] Field of Search ............................. 324/318, 322, 324/300, 306, 307, 309, 314; 600/424, 423, 422, 421

[56] References Cited

U.S. PATENT DOCUMENTS

| | | | |
|---|---|---|---|
| 4,629,989 | 12/1986 | Riehl et al. ................... | 324/318 |
| 5,365,927 | 11/1994 | Roemer et al. ................ | 324/309 |
| 5,664,234 | 9/1997 | Rasche et al. ................. | 324/318 |
| 5,715,822 | 2/1998 | Watkins et al. ............... | 128/653.5 |
| 5,722,410 | 3/1998 | NessAiver ..................... | 128/653.5 |

*Primary Examiner*—Louis Arana
*Attorney, Agent, or Firm*—Hill & Simpson

[57] ABSTRACT

In a method for determining the position of at least one local antenna in an examination chamber of a magnetic resonance apparatus, magnetic resonance signals emitted by a body arranged in the examination chamber are received, locus-encoded in at least one coordinate direction, by an antenna that has a homogeneous sensitivity distribution. From the received magnetic resonance signals, image data that are locus-resolved in the at least one coordinate direction are produced in the form of first intensity values. Magnetic resonance signals emitted by the body are received, locus-encoded in the coordinate direction, by the at least one local antenna. From the received magnetic resonance signals, image data that are locus-resolved in the at least one coordinate direction are produced in the form of second intensity values. From the second intensity values, normalized intensity values are formed by relating the second intensity values respectively to the first intensity values belonging to the same coordinate values. The normalized intensity values are searched for their largest value. A coordinate value that belongs to the largest normalized intensity value indicates the position of the at least one local antenna in the coordinate direction.

7 Claims, 4 Drawing Sheets

METHOD FOR DETERMINING THE POSITION OF A LOCAL ANTENNA IN AN EXAMINATION CHAMBER OF A MAGNETIC RESONANCE APPARATUS

BACKGROUND OF THE INVENTION

1. Field of the Invention

The present invention relates to a method for determining the position of at least one local antenna in an examination chamber of a magnetic resonance apparatus.

2. Description of the Prior Art

In a diagnostic magnetic resonance apparatus, a local antenna is used for improvement of the signal-noise ratio. Such an antenna is matched to the size of the body region to be examined. Local antenna as known, for example, that are built fixedly into the patient table or engaged at fixed positions on the patient table for examination of the spinal column or for examination of the female breast. Also known are local antennas which are freely movable in the examination chamber, for example, flexible antennas, wrap-around antennas and extremity antennas.

The positioning of local antennas in the examination chamber of the magnetic resonance apparatus has until now ensued in most cases by means of a light-beam localizer that is fastened to the magnetic resonance apparatus at a defined distance to the center of the examination chamber. A suitable light-beam localizer is, for example, described in U.S. Pat. No. 4,629,989. After the local antenna has been applied to the patient at an optimal distance from the region under examination, the patient is positioned with the local antenna so that the center of the local antenna coincides with a light mark of the light-beam localizer. Subsequently, the patient is moved into the center of the examination chamber by the defined distance predetermined by the location of the light-beam localizer. In such a known magnetic resonance apparatus, the acquisition of the position of the local antenna is limited to the coordinate that is changeable due to the path of travel of the patient table. In the examination chamber, no further acquisition of the local antenna position ensues.

German OS 44 38 584 describes a display arrangement together with a magnetic resonance imaging apparatus, which indicates a position and an orientation of a plane in which an image is to be obtained. The display arrangement is movable, and includes a radio-frequency transmitter with several transmission coils. A tracking unit has several reception coils that receive the signal emitted by the transmission coils. From this, the tracking unit determines the location of the transmission coils.

SUMMARY OF THE INVENTION

An object of the present invention is provide a method with which the position of a local antenna in the examination chamber of a magnetic resonance apparatus can be determined.

The object is achieved in a method in accordance with the invention including the following steps. Magnetic resonance signals are emitted by a body arranged in the examination chamber and are received, locus-encoded for at least one coordinate direction, by an antenna that has a homogeneous sensitivity distribution. From the received magnetic resonance signals, locus-resolved image data in the at least one coordinate direction are produced in the form of first intensity values. Magnetic resonance signals emitted by the body are received, locus-encoded in the aforementioned coordinate direction, by at least one local antenna. From the received magnetic resonance signals, image data that are locus-resolved in the at least one coordinate direction are produced in the form of second intensity values. From the second intensity values, normalized intensity values are formed by relating the respective second intensity values and the first intensity values belonging to the same coordinate values. The normalized intensity values are searched for their largest value. A coordinate value that belongs to the largest normalized intensity value indicates the position of the at least one local antenna in the coordinate direction.

By normalizing the second intensity values, image data concerning anatomical details are removed. There remain only image data identifying the sensitivity distribution of the local antenna, which are then evaluated in order to determine the position.

The method is of particular advantage when several local antennas are used simultaneously in a magnetic resonance apparatus, e.g. in the form of an antenna array. The position of each local antenna can then be determined, and can be communicated to the process control computer of the magnetic resonance apparatus. The positions of the local antennas are, for example, used to select one of the local antennas that supplies the highest possible signal-noise ratio for a particular body region, and thus the best resolution. This antenna selection can then ensue automatically.

In another embodiment, spatial projections of the body are evaluated as the image data. In order to produce the spatial projections, locus-encoding with a gradient field in the corresponding coordinate direction thereby suffices. In this way, the position of the local antenna in this coordinate direction can be determined rapidly and with sufficient precision.

In a further embodiment several local antennas are present that receive the magnetic resonance signals simultaneously and, from the received magnetic resonance signals of each local antenna, image data, respectively locus-resolved in the coordinate direction, are produced in the form of second intensity values allocated to the local antennas. In this particularly time-saving method for determining the position of several local antennas, it is assumed that the magnetic resonance apparatus has several signal processing channels connected with the individual local antennas.

The search for the maximum intensity value is simplified if according to a further embodiment the intensity values are spatially smoothed or filtered. The spatial curve of the intensity values is often overlaid with noise. After removal of the noise portions, the maximum of the intensity distribution can be determined with a high degree of certainty. In comparison to a multiple measurement with subsequent average value formation, filtering has the advantage that only one measurement need be carried out, resulting in a considerable savings of time in the determination of the position.

In another embodiment the first and second intensity values are normalized to the same noise power before the production of the aforementioned normalized intensity values. By means of a comparison of the intensity values, normalized to the same noise power, of the individual local antennas, it can be estimated which local antenna has the best signal-noise ratio for a particular examination region. For such information, not only is the position of the center of the local antenna important, but also the signal-noise ratio of the antennas themselves.

DESCRIPTION OF THE PREFERRED EMBODIMENTS

Figure 1:
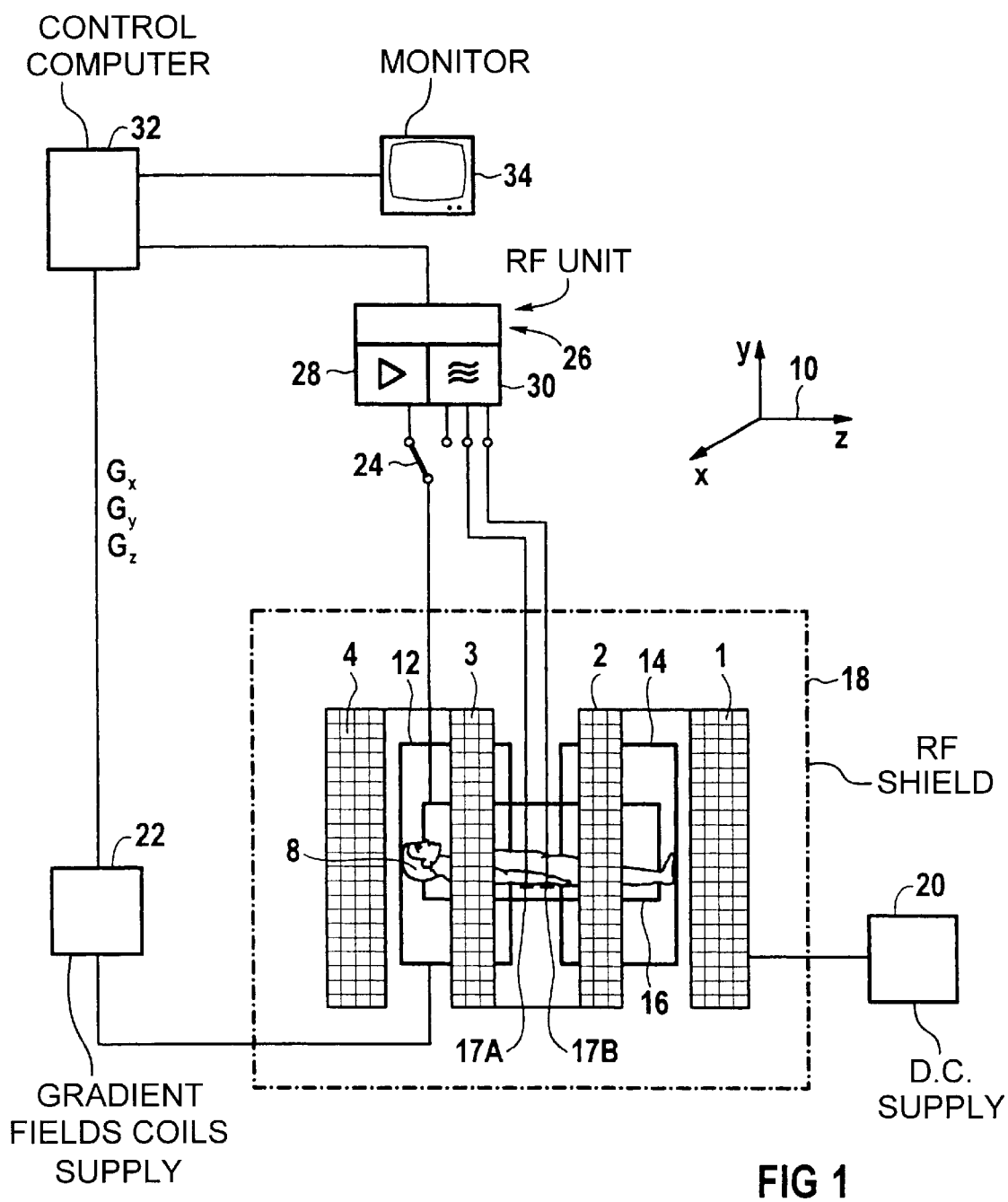
FIG. 1 is a schematic overview of the basic components of a diagnostic magnetic resonance apparatus, in which the inventive method can be used.

FIG. 1 shows an overview of a diagnostic magnetic resonance apparatus, with which anatomical tomograms and angiograms of the human body can be produced, or with which functional examinations can be carried out. The magnetic resonance apparatus comprises coils 1 to 4, which produce in their interior space a nearly homogeneous magnetic basic field in the axial direction in a volume under examination, with high field strength. In the case of medical diagnosis, a part to be examined of a patient 8 is also located in the volume under examination. A gradient coil system, for producing independent additional magnetic fields likewise in the direction of the main magnetic field, is allocated to the volume under examination. The additional magnetic fields have are gradient fields respectively having magnetic field gradients which are perpendicular to one another in the x, y and z directions according to a Cartesian coordinate system 10. In FIG. 1, for the sake of clarity only gradient coils 12 and 14 are shown, which, together with a pair of opposed gradient coils of the same type, serve for the production of a gradient in the x direction. Coils of the same type (not shown here) for producing a gradient field in the y direction are positioned parallel to the patient 8, above and below the patient. Gradient coils for producing the gradient field in the z direction are positioned transverse to the longitudinal axis of the patient 8 at the head end and at the foot end.

The magnetic resonance apparatus also includes a radio-frequency antenna 16 used for producing and receiving magnetic resonance signals, which, as a whole-body antenna, in the reception mode, has a homogeneous sensitivity in the volume under examination. In addition, local antennas 17A and 17B are present, which are here fashioned as part of an antenna array for the examination of the spinal column.

The coils 1 to 4, bounded by a broken line 18, the gradient coil system and the radio-frequency antennas represent the actual examination apparatus, which must be largely free of disturbing signals and is surrounded by a radio-frequency shielding. The broken line 18 symbolizes the radio-frequency shielding.

The remaining components of the magnetic resonance apparatus are arranged outside the radio-frequency shielding 18. For the operation of the magnetic coils 1 to 4, a direct-current power supply unit 20 is provided. A gradient power supply 22 supplies the gradient coil system with the currents required to set up and dismantle the gradient fields. The gradient power supply 22 and the gradient coil system together form the gradient system of the magnetic resonance apparatus. Via a duplexer 24 (shown as a switch), the radio-frequency antenna 16 is connected with a radio-frequency unit 26 for signal production and reception. The radio-frequency unit 26 includes receiver amplifiers 28 and a radio-frequency transmitter 30. The local antennas 17A, 17B are connected directly to separate receive channels of the radio-frequency means 16. The operation of the magnetic resonance apparatus is controlled by a control computer 32, to which a monitor 34 is connected, if warranted, via an image computer (not further shown). The control computer 32 produces, among other things, target values of the gradient field, designated $G_x$, $G_y$, and $G_z$. The localization method, specified in detail below, also runs in the control computer 32.

Figure 2:
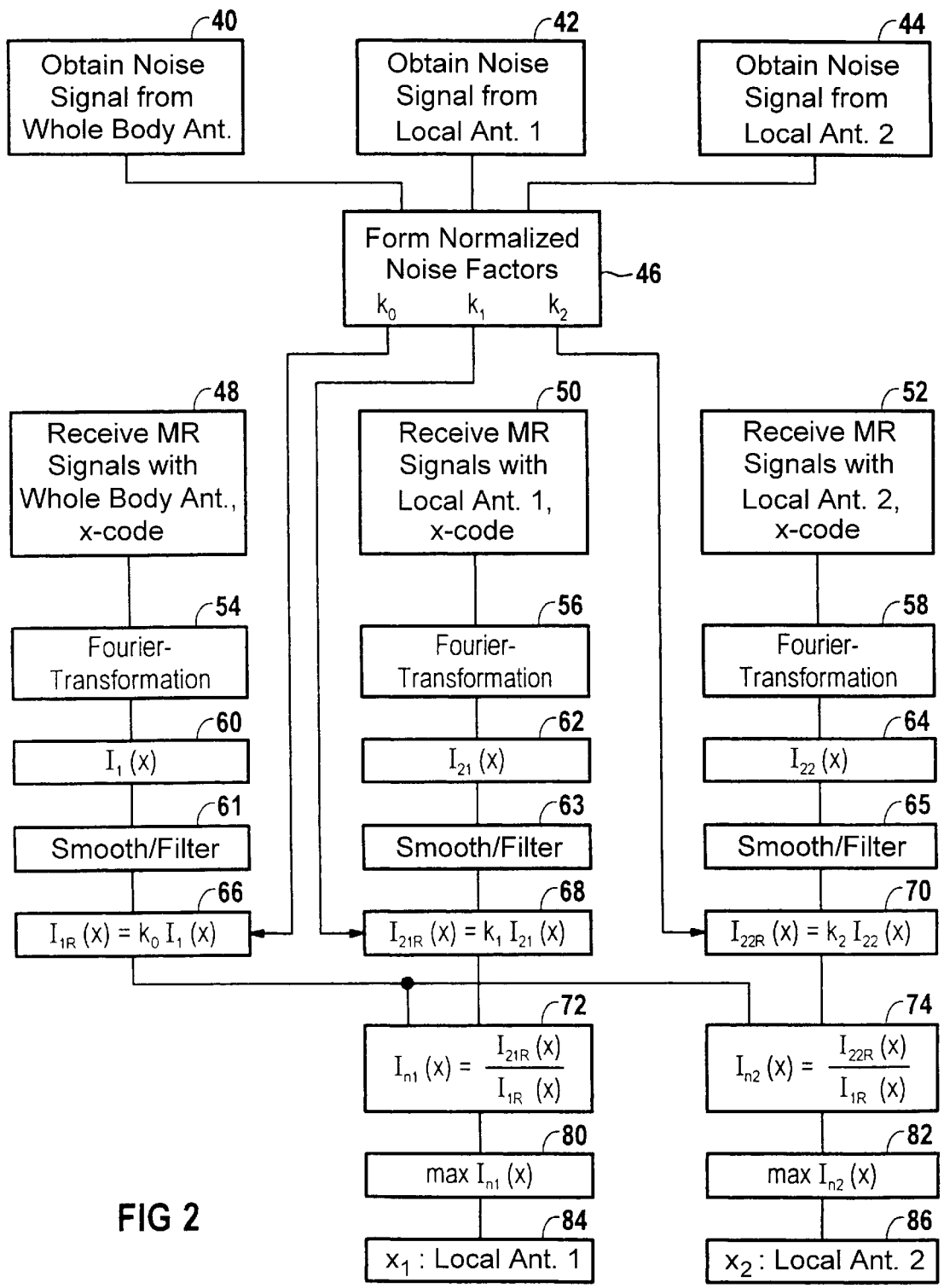
FIG. 2 shows a diagram with the individual steps for determining the position of two local antennas, in accordance with the inventive method.

The localization method is composed of the method steps shown in overview in FIG. 2. After the patient 8 to be examined is positioned on a patient table outside the magnetic resonance apparatus, the patient table with the patient is moved into the examination chamber of the magnetic resonance apparatus. First, noise is recorded with the whole-body antenna 16 and the local antennas 17A and 17B, without previous excitation of the magnetic resonance and without gradient fields. The noise signal emitted at the output of the individual measurement channels is composed of noise contributions emitted by the patient and received by the antennas 16, 17A and 17B, and noise contributions produced in the receive channels, in particular in the preamplifiers. The determination of these noise signals is identified with the reference character 40 in FIG. 2 for the whole-body antenna 16, and with the reference characters 42 or 44 for the local antennas 17A and 17B. From the recorded noise signals 40, 42 and 44, an average noise power is determined, in order to determine therefrom noise normalization factors $k_0$ for the whole-body antenna channel, $k_1$ for the first local antenna channel and $k_2$ for the second local antenna channel (method step 46). As explained below, subsequently processed measurement values of the antennas 16, 17A and 17B are normalized to the same noise power using the noise normalization factors $k_0$, $k_1$, $k_2$.

The actual method for determining the position begins with an excitation of the body 8 positioned in the volume under examination, by emitting a radio-frequency pulse by means of the whole-body antenna. After the excitation, the signal emitted by the body is received, locus-encoded in one coordinate direction with a gradient field produced by the gradient coils. In FIG. 2, the reception with the whole-body antenna takes place in step 48, the reception of the first local antenna 17A takes place in step 50 and the reception of the second local antenna 17B takes place in step 52. The reception ensues simultaneously for all radio-frequency antennas 16, 17A and 17B. As an example, in FIG. 2 a locus-encoding in the x-direction is indicated. The locus-encoding can ensue, however, in an arbitrary coordinate direction, and even in an arbitrary spatial direction, by means of corresponding gradient fields.

Since, in the case under consideration, the locus-encoding is mirrored in the frequency spectrum, the received magnetic resonance signals are subjected to a Fourier transformation in steps 54, 56 and 58. Intensity values are determined after absolute value formation of the amplitude values belonging to the individual frequencies, dependent on the corresponding coordinate values in the previously locus-encoded coordinate direction. The magnetic resonance signals received with the whole-body antenna 16 result in first intensity values $I_1(x)$ (step 60). The magnetic resonance signals received by the first local antenna 17A result in second intensity values $I_{21}(x)$ (step 62), and the magnetic resonance signals received by the second local antenna 17B result in second intensity values $I_{22}(x)$ (step 64). The intensity values $I_1(x)$, $I_{21}(x)$, $I_{22}(x)$ represent spatial projections from slices of the body 8, which are oriented perpendicular to the coordinate direction. These spatial projections are respectively smoothed or subjected to a lowpass filtering in steps 61, 63 and 65, and are then normalized to the same noise power with the previously determined noise normalization factors, in order to form noise-normalized intensity values. The noise-normalized intensity values are identified with the additional index R. For the whole-body antenna 16, there accordingly result noise-normalized intensity values $I_{1R}(x)$ (step 66); for the first local antenna 17A there accordingly result noise-normalized second intensity values $I_{21R}(x)$ (step 68); and for the second local antenna 17B there result noise-normalized second intensity values $I_{22R}(x)$ (step 70).

In order to eliminate variations arising from the body 8 in the intensity values $I_{21R}(x)$ and $I_{22R}(x)$ in the coordinate direction from the intensity values $I_{21R}(x)$ and $I_{22R}(x)$ determined using the local antennas 17A and 17B, the noise-normalized second intensity values for each coordinate value x are related to the corresponding first noise-normalized intensity value $I_{1R}(x)$. For the magnetic resonance signals recorded with the first local antenna 17A, normalized intensity values $I_{n1}(x)$ result (step 72), and for the magnetic resonance signals recorded with the second local antenna, normalized intensity values $I_{n2}(x)$ (method step 74). The normalized intensity values $I_{n1}(x)$ and $I_{n2}(x)$ are respectively searched for their maximum. For the normalized intensity values $I_{n1}(x)$ belonging to the first local antenna 17A, this ensues in step 80, and for the intensity values $I_{n2}(x)$ belonging to the second local antenna 17B this ensues in step 82. The coordinate value x1, x2 belonging to the maximum intensity value indicates the position of the local antenna 17A or 17B in the corresponding coordinate direction. In FIG. 2, this is identified with the reference character 84 for the first local antenna 17A, and is identified with the reference character 86 for the second local antenna 17B.

If the positions of the local antennas in further coordinate directions, e.g. in the y-direction or the z-direction, are to be determined, magnetic resonance signals locus-encoded in the desired coordinate direction are correspondingly received and evaluated. This ensues by means of the application of a gradient field in the corresponding coordinate direction during the reception.

Alongside the evaluation of spatial projections, it is likewise possible to search tomograms for an intensity maximum. If the local antennas 17A, 17B are for example arranged in an x-y plane, tomograms parallel to this plane are recorded by each local antenna 17A, 17B. Here as well, for the elimination of image information arising from the body 8, the tomograms recorded with the local antennas 17A, 17B are normalized to a corresponding tomogram recorded by the whole-body antenna. The coordinate values belonging to the intensity maximum in the normalized images, e.g. $x_1$, $y_1$ and $x_2$, $y_2$, then indicate the position of the local antennas 17A, 17B in the corresponding image planes.

According to an analogous method, intensity values of a volume that were produced e.g. in the form of a 3D data set can be searched for an intensity maximum in order to determine the center of a local antenna.

Figure 3:
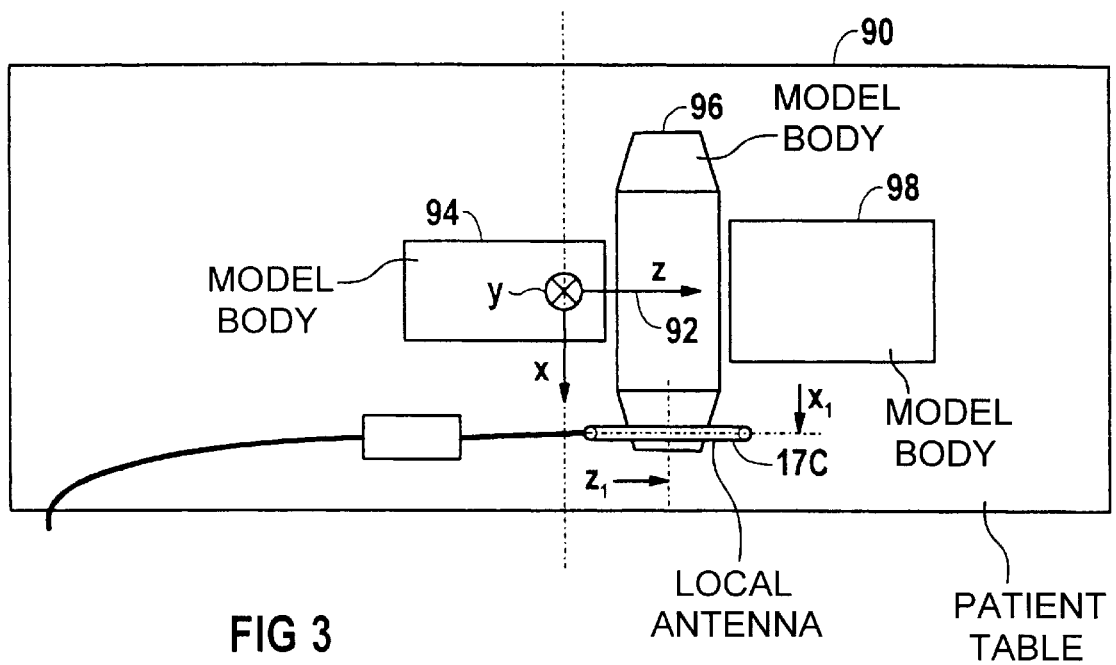
FIG. 3 shows a top view of a measurement arrangement for checking the precision of the position determination method, in accordance with the inventive method.
Figure 4:
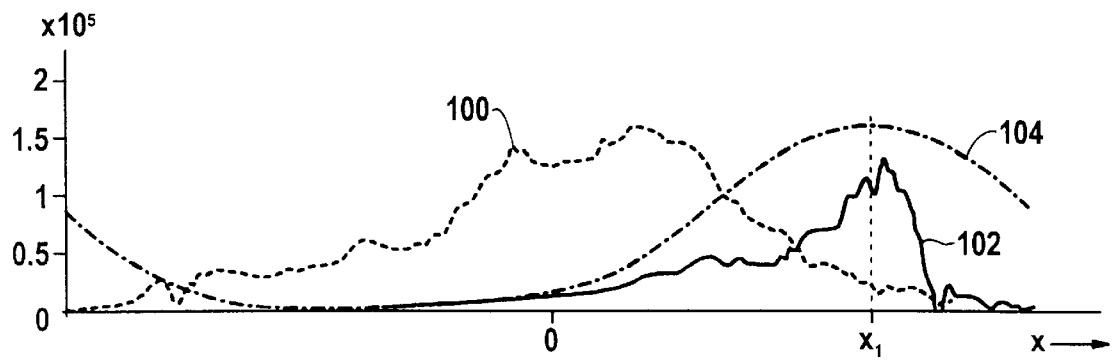
FIG. 4 shows intensity values resolved in a first coordinate direction, which were determined using the measurement arrangement according to FIG. 3, in accordance with the inventive method.
Figure 5:
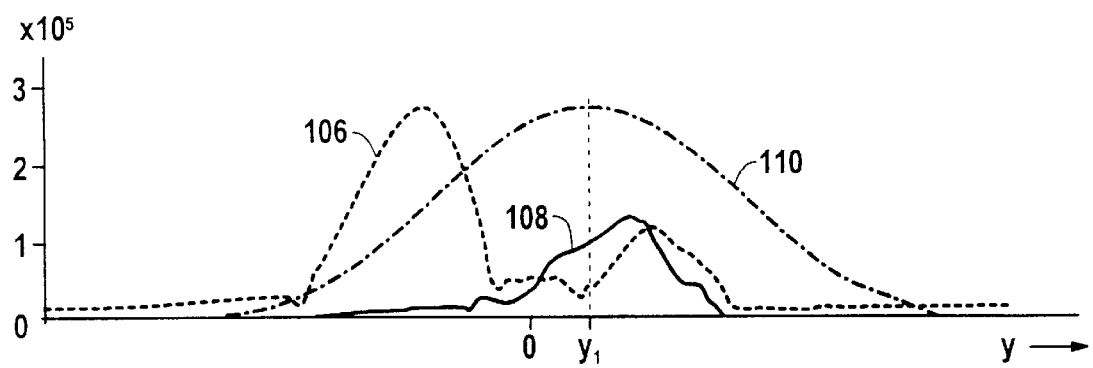
FIG. 5 shows intensity values locus-resolved in a second coordinate direction, which were determined using the measurement arrangement according to FIG. 3.
Figure 6:
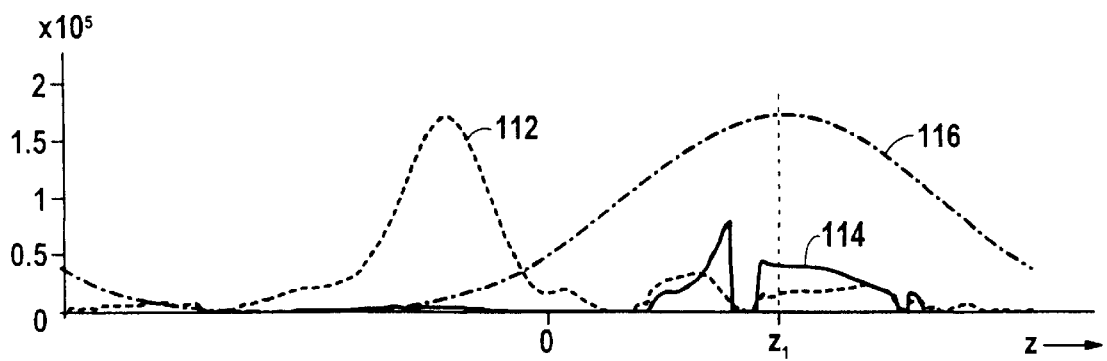
FIG. 6 shows intensity values locus-resolved in a third coordinate direction, which were determined using the measurement arrangement according to FIG. 3.

FIG. 3 shows a measurement antenna with a model body, by means of which the position of a movable local antenna is determined. FIGS. 4 to 6 show the intensity values dependent on location that are thereby determined. The center of a rectangular coordinate system 92 is located in the middle of a positioning surface of a patient table 90. On the positioning surface, there are arranged three different model bodies 94, 96, 98 made of a material that can be detected with magnetic resonance technology, such as e.g. Plexiglas containers filled with a saline solution (measurement phantoms). The first model body 94 is fashioned cylindrically, whereby the longitudinal axis of the model body 94 coincides with the longitudinal axis of the patient table 90. The second model body 96 is of oblong construction, with an oval cross-section and tapering ends. The longitudinal axis of the second body 96 stands perpendicular to the longitudinal axis of the patient table 90. The third model body 98 is connected to the second body 96, which like the first body 94 is fashioned cylindrically, but has larger overall outer dimensions. A movable, i.e. freely applicable local antenna 17C is to be localized. The local antenna 17C has a circular antenna conductor loop, whose midpoint is located at the coordinate values $x_1$, $y_1$, and $z_1$. The antenna conductor loop of the local antenna 17C surrounds one end of the second body 96, whereby the antenna axis coincides with the longitudinal axis of the second body 96.

FIG. 4 shows, dependent on the locus coordinate x, first intensity values 100, which represent spatial projections of the model bodies 94, 96, 98 along the x-coordinate direction, and which were produced from the received signals of the whole-body antenna 16. Uniformly locus-encoded magnetic resonance signals are received with the local antenna 17C and are converted into second intensity values 102. The second intensity values 102 are now normalized to the first intensity values 100 and are subsequently subjected to a spatial smoothing. The result of the spatially smoothed, normalized intensity values is shown in FIG. 4 as a broken line 104. The coordinate value x, belonging to the maximum intensity value indicates the position of the intensity maximum of the local antenna 17C in the x-coordinate direction.

FIG. 5 shows, analogously to FIG. 4, spatial projections along the y-direction. The reference character 106 identifies the first intensity values, which are produced from magnetic resonance signals that were received by the whole-body antenna 16. The magnetic resonance signals locus-encoded in the y-direction by the local antenna 17C are processed to form second intensity values 108. Here as well, the second intensity values 108 are normalized to the first intensity values 106. The result of the normalization is represented by a broken curve 110. The coordinate value $y_1$ belonging to the maximum normalized intensity value indicates the maximum sensitivity of the local antenna 17C in the y-coordinate direction.

Correspondingly, FIG. 6 shows, in dependence in the z-coordinate direction, first intensity values 112 of the whole-body antenna and second intensity values 114 of the local antenna 17C and normalized intensity values 116.

The relative precision of the localization of the center of the local antenna 17C is from a tenth to a twentieth of the diameter of the antenna conductor loop. For example, given a local antenna 17C with a diameter of 20 cm, a precision of localization of from 1 to 2 cm results. From FIGS. 4 to 6, it can be seen that a determination of the maximum directly from the second intensity values 102, 108, 114, without normalizing to the intensity values 100 or 106 or 112 produced by the whole-body antenna 16, yields a considerably less precise localization result.

Although modifications and changes may be suggested by those skilled in the art, it is the intention of the inventor to embody within the patent warranted hereon all changes and modifications as reasonably and properly come within the scope of his contribution to the art.

I claim as my invention:

1. A method for determining a position of at least one local antenna in an examination chamber of a magnetic resonance apparatus, comprising the steps of:

receiving magnetic resonance signals, emitted by a subject disposed in an examination chamber using an antenna disposed in said examination chamber having a homogenous sensitivity distribution, and locus-encoding said magnetic resonance signals in at least one coordinate direction to obtain locus-encoded signals;

from said locus-encoded signals, obtaining image data, in a form of first intensity values, locus-resolved in said at least one coordinate direction;

receiving magnetic resonance signals emitted by said subject using at least one local antenna disposed in said examination chamber, and locus-encoding said magnetic resonance signals received by said at least one local antenna to obtain local antenna locus-encoded signals;

from said local antenna locus-encoded signals, obtaining image data, in a form of second intensity values, locus-resolved in said at least one coordinate direction, said second intensity values respectively having coordinate values associated therewith;

from said second intensity values, forming normalized intensity values by relating said second intensity values respectively to said first intensity values having the same respective coordinate values;

searching said normalized intensity values for a largest normalized intensity value, said first intensity values respectively having coordinate values associated therewith; and selecting a coordinate value associated with said largest normalized intensity value as an identification of the position of said at least one local antenna in said at least one coordinate direction.

2. A method as claimed in claim 1 wherein said image data from which said first and second intensity values are formed comprise spatial projections of said subject.

3. A method as claimed in claim 1 wherein said image data from which said first and second intensity values are formed comprise tomography information.

4. A method as claimed in claim 1 for use with a plurality of local antennas in said examination chamber which simultaneously receive said magnetic resonance signals from said subject, and wherein a set of second intensity values is produced for each local antenna in said plurality of local antennas, with each set of second intensity values being allocated to the local antenna which produced the set of second intensity values.

5. A method as claimed in claim 1 comprising the additional step of spatially smoothing said first and second intensity values.

6. A method as claimed in claim 1 comprising the additional step of filtering said first and second intensity values.

7. A method as claimed in claim 1 comprising the additional steps of:

forming first raw intensity values from said locus-encoded signals obtained from said antenna having a homogenous sensitivity distribution, and normalizing said first raw intensity values to a noise power to produce said first intensity values; and producing second raw intensity values from said local antenna locus-encoded signal, and normalizing said second raw intensity values to said noise power to produce said second intensity values.

* * * * *